(12) United States Patent
Lui et al.

(10) Patent No.: US 10,967,192 B2
(45) Date of Patent: Apr. 6, 2021

(54) SYSTEMS AND METHODS FOR CHARGING A MEDICAL DEVICE IMPLANTED INTO A PATIENT

(71) Applicant: Boston Scientific Neuromodulation Corporation, Valencia, CA (US)

(72) Inventors: Mun Pook Lui, Northridge, CA (US); Erin Suzanne Roper, Sherman Oaks, CA (US); Joey Chen, Valencia, CA (US); Gaurav Gupta, Valencia, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 93 days.

(21) Appl. No.: 16/230,911

(22) Filed: Dec. 21, 2018

(65) Prior Publication Data
US 2019/0201700 A1     Jul. 4, 2019

Related U.S. Application Data

(60) Provisional application No. 62/612,229, filed on Dec. 29, 2017.

(51) Int. Cl.
| | |
|---|---|
| *A61N 1/37* | (2006.01) |
| *A61N 1/378* | (2006.01) |
| *A61B 5/00* | (2006.01) |
| *A61N 1/08* | (2006.01) |
| *A61N 1/372* | (2006.01) |
| *H02J 7/00* | (2006.01) |

(52) U.S. Cl.
CPC .......... *A61N 1/3787* (2013.01); *A61B 5/6831* (2013.01); *A61N 1/08* (2013.01); *A61B 5/0031* (2013.01); *A61B 5/6844* (2013.01); *A61B 2560/0219* (2013.01); *A61N 1/37217* (2013.01); *A61N 1/37247* (2013.01); *H02J 7/00* (2013.01)

(58) Field of Classification Search
CPC .............. A61N 1/3787; A61N 1/37229; A61N 1/37247; A61B 2560/0219
See application file for complete search history.

(56) References Cited

U.S. PATENT DOCUMENTS

| | | | |
|---|---|---|---|
| 4,143,661 A * | 3/1979 | LaForge | ............... A61N 1/3787 607/61 |
| 5,193,539 A | 3/1993 | Schulman et al. | |
| 5,193,540 A | 3/1993 | Schulman et al. | |

(Continued)

*Primary Examiner* — Eric D. Bertram
(74) *Attorney, Agent, or Firm* — Branch Partners PLLC; Bruce E. Black

(57) ABSTRACT

A wearable article for receiving and retaining a charger for charging a medical device implanted into a patient includes a coil-assembly cavity and first and second controller cavities defined between first and second major surfaces of a body of the wearable article. The coil-assembly cavity is configured to retain a coil assembly of the charger, and the first and second controller cavities are each configured to receive at least a portion of a controller of the charger. A controller slit is defined along the first major surface and is open to both the first and second controller cavities. The first controller cavity is configured to receive at least a portion of the controller with a user interface of the controller extending or observable through the controller slit or disposed in the second controller cavity.

19 Claims, 11 Drawing Sheets

(56) References Cited

U.S. PATENT DOCUMENTS

| | | |
|---|---|---|
| 5,312,439 A | 5/1994 | Loeb |
| 5,324,316 A | 6/1994 | Schulman et al. |
| 5,405,367 A | 4/1995 | Schulman et al. |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 7,244,150 B1 | 7/2007 | Brase et al. |
| 7,450,997 B1 | 11/2008 | Pianca et al. |
| 7,660,631 B2 | 2/2010 | Whitehurst et al. |
| 7,672,734 B2 | 3/2010 | Anderson et al. |
| 7,738,965 B2 * | 6/2010 | Phillips ................ A61N 1/3787 607/61 |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,925,357 B2 | 4/2011 | Phillips et al. |
| 7,949,395 B2 | 5/2011 | Kuzma |
| 7,974,706 B2 | 7/2011 | Moffitt et al. |
| 8,175,710 B2 | 5/2012 | He |
| 8,214,048 B1 | 7/2012 | Whitehurst et al. |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,626,297 B2 | 1/2014 | Jaax et al. |
| 8,688,235 B1 | 4/2014 | Pianca et al. |
| 9,216,311 B2 | 12/2015 | Champion |
| 9,283,394 B2 | 3/2016 | Whitehurst et al. |
| 9,407,110 B2 * | 8/2016 | Lui ........................ H02J 7/025 |
| 2005/0113887 A1 * | 5/2005 | Bauhahn ............. A61N 1/3787 607/61 |
| 2005/0288743 A1 * | 12/2005 | Ahn ..................... A61N 1/3787 607/61 |
| 2006/0036286 A1 | 2/2006 | Whitehurst et al. |
| 2007/0150036 A1 | 6/2007 | Anderson |
| 2009/0082835 A1 * | 3/2009 | Jaax .................. H02J 7/007192 607/61 |
| 2009/0187222 A1 | 7/2009 | Barker |
| 2009/0276021 A1 | 11/2009 | Meadows et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0048687 A1 * | 2/2013 | Do ........................... A41F 9/00 224/222 |
| 2013/0105071 A1 | 5/2013 | DiGiore et al. |
| 2013/0197602 A1 | 8/2013 | Pianca et al. |
| 2014/0114373 A1 * | 4/2014 | Aghassian ........... H04B 5/0081 607/45 |

\* cited by examiner

SYSTEMS AND METHODS FOR CHARGING A MEDICAL DEVICE IMPLANTED INTO A PATIENT

CROSS-REFERENCE TO RELATED APPLICATIONS

This application claims the benefit under 35 U.S.C. § 119(e) of U.S. Provisional Patent Application Ser. No. 62/612,229, filed Dec. 29, 2017, which is incorporated herein by reference.

FIELD

The present invention is directed to the area of implantable medical devices, and in particular, to wearable systems and devices for retaining chargers for recharging electrical systems of implanted medical devices, as well as methods of making and using the wearable systems and devices.

BACKGROUND

Implantable medical devices, such as electrical stimulation systems, have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

In some aspects, a wearable article for receiving and retaining a charger for charging a medical device implanted into a patient, where the charger includes a coil assembly and a controller with a user interface, includes a body. The body has an elongated shape with a longitudinal length, a first major surface, and an opposing second major surface. The first major surface is configured for facing outwardly from the patient when the wearable article is worn by the patient. A coil-assembly cavity is defined in the body between the first major surface and the second major surface and is configured to retain the coil assembly. A first controller cavity is defined in the body between the first major surface and the second major surface and is configured to receive at least a portion of the controller. A second controller cavity is defined in the body between the first major surface and the second major surface and is configured to receive at least a portion of the controller. A controller slit is defined along the first major surface and is open to both the first controller cavity and the second controller cavity. The first controller cavity is configured to receive at least a portion of the controller with the user interface extending or observable through the controller slit or disposed in the second controller cavity.

In at least some embodiments, the first and second controller cavities are positioned along the body so that they are both disposed along an anterior portion of the patient when the wearable article is worn by the patient with the coil-assembly cavity positioned at least partially over a medical device implanted in the patient.

In at least some embodiments, the coil-assembly cavity permanently retains the coil assembly. In at least some embodiments, the coil-assembly cavity is configured to removably retain the coil assembly. In at least some embodiments, the wearable article further defines a coil-assembly slit, the coil-assembly slit open to the coil-assembly cavity and configured to enable the coil assembly to pass through the coil-assembly slit and into the coil-assembly cavity. In at least some embodiments, the coil-assembly slit is defined along the first major surface. In at least some embodiments, the coil-assembly slit is defined along the second major surface.

In at least some embodiments, the coil-assembly cavity is a first coil-assembly cavity, and the wearable article further includes a second coil-assembly cavity offset from the first coil-assembly cavity along the longitudinal length of the belt, the second coil-assembly cavity configured to retain the coil assembly. In at least some embodiments, the wearable article further includes a coil-assembly slit open to each of the first coil-assembly cavity and the second coil-assembly cavity, and configured to enable the coil assembly to pass through the coil-assembly slit and into either the first coil-assembly cavity or the second coil-assembly cavity.

In at least some embodiments, at least one of the first major surface or the second major surface of the body along the coil-assembly cavity is formed from a mesh material. In at least some embodiments, at least one of the first major surface or the second major surface of the body along the coil-assembly cavity is formed from performance knit fabric. In at least some embodiments, the body is configured to stretch by no less than 4% and no more than 12% along a longitudinal length of the body.

In at least some embodiments, the body has an elliptical shape. In at least some embodiments, the controller slit is disposed along a longitudinal seam extending along the longitudinal length of the body along the first major surface. In at least some embodiments, the body is symmetrical about the longitudinal seam.

In other aspects, a charging system for charging a medical device implanted into a patient includes any of the above-described wearable articles and a charger configured for being retained by the wearable article. The charger includes a coil assembly and a controller coupleable with the coil assembly. The controller includes a battery and a user interface. The first controller cavity of the wearable article is configured to receive at least a portion of the controller with the user interface extending or observable through the controller slit or disposed in the second controller cavity of the wearable article.

In at least some embodiments, the first major surface of the wearable article defines one or more utility apertures positioned in proximity to the first controller cavity of the wearable article, the one or more utility apertures configured to receive a cable from a location external to the wearable article and enable the cable to couple with the controller to charge the controller battery while the controller is at least partially retained in the first controller cavity.

In at least some embodiments, the first major surface of the wearable article defines one or more perforated regions positioned in proximity to the second controller cavity of the wearable article, the one or more perforated regions configured to facilitate the patient hearing audible signals output from the user interface of the controller.

In yet other aspects, a charging system for charging a medical device implanted into a patient includes a charger configured for charging the medical device. The charger includes a coil assembly and a controller coupleable with the coil assembly. The controller includes a battery and a user interface. A wearable article is configured for retaining the charger. The wearable article includes a body having an elongated shape. A coil-assembly cavity is defined in the body and is configured to retain the coil assembly. At least one controller cavity is configured to retain at least a portion of the controller. The at least one controller cavity is defined in the body remote from the coil-assembly cavity to separate the battery from the coil assembly to limit heating in the battery. In at least some embodiments, the charger further includes a charger cable configured to couple the controller to the coil assembly, the charger cable permanently retained within the body of the wearable article.

In still yet other aspects, a method for charging a medical device implanted in a patient includes providing any of the above-described charging systems. The controller is inserted into a first controller cavity of the at least one controller cavity with the user interface extending or observable through a controller slit open to the first controller cavity or disposed in a second controller cavity of the at least one controller cavity. The controller is coupled to the coil assembly. The wearable article is donned with the coil assembly positioned over the implanted medical device.

In at least some embodiments, donning the wearable article with the coil assembly positioned over the implanted medical device includes positioning the controller along an anterior portion of the patient. In at least some embodiments, donning the wearable article with the coil assembly positioned over the implanted medical device includes positioning the controller along an anterior portion of the patient while also positioning the coil assembly along a posterior portion of the patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
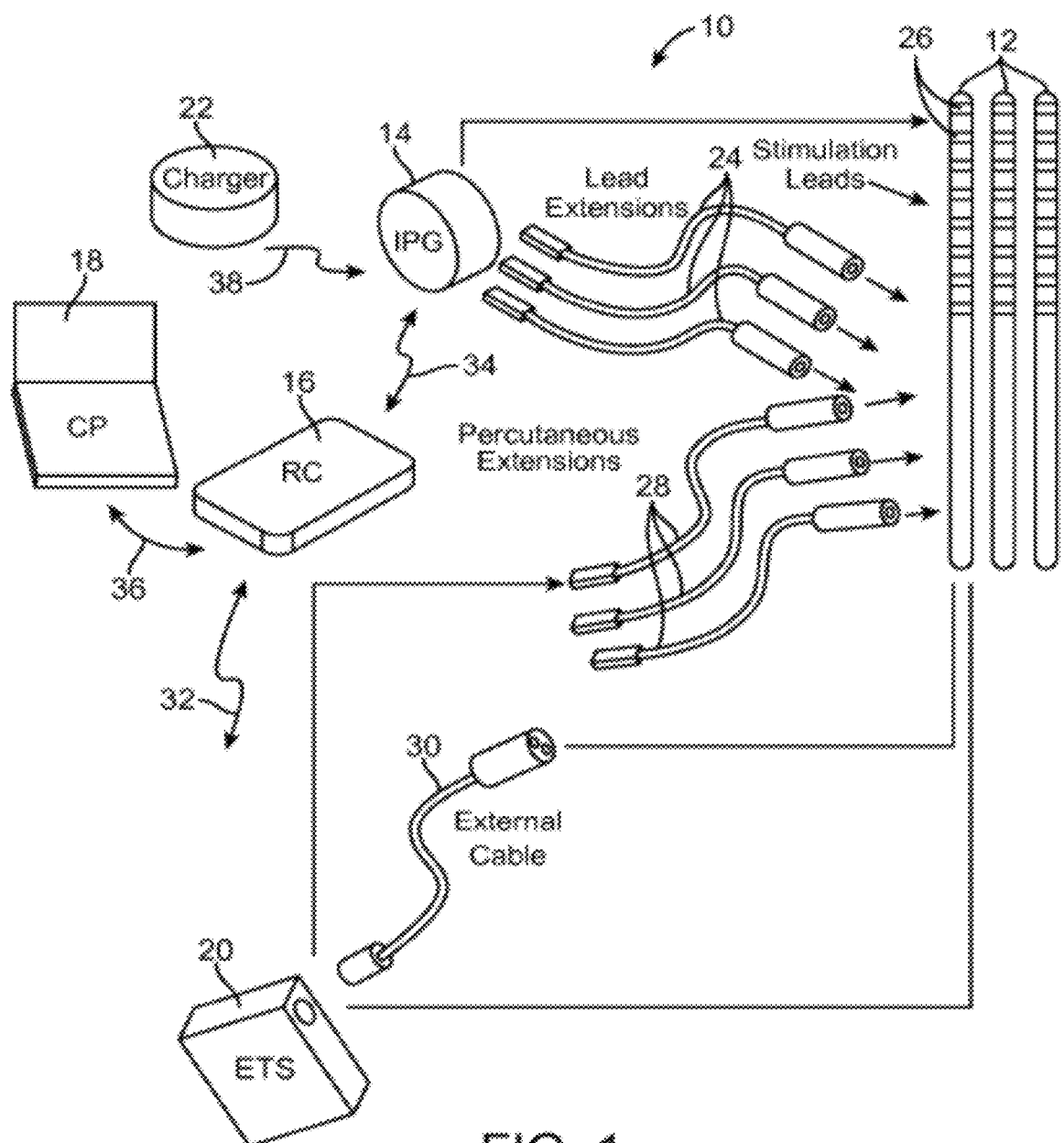
FIG. 1 is a schematic view of one embodiment of an electrical stimulation system, according to the invention.

The present invention is directed to the area of implantable medical devices, and in particular, to wearable systems and devices for retaining chargers for recharging electrical systems of implanted medical devices, as well as methods of making and using the wearable systems and devices.

Although useful in conjunction with a broad range of different types of implantable medical devices, the below-described invention will be described in conjunction with implantable electrical stimulation systems. In particular, spinal cord stimulation systems with percutaneous leads. It will be understood that describing the invention with respect to spinal cord stimulation systems is for clarity of description only, and is not meant to be limiting.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Suitable implantable electrical stimulation systems may also include one or more microstimulators, which include an implantable control module containing electrical circuitry connected to one or more electrodes that extend through, or along, one or more walls of the control module. In some instances, microstimulators include segmented electrodes. Examples of microstimulators are found in, for example, U.S. Pat. Nos. 5,193,539; 5,193,540; 5,312,439; 5,324,316; 5,405,367; 7,660,631; 8,214,048; 9,283,394; and U.S. Patent Applications Publication No. 2006/0036286, all of which are incorporated by reference.

In the discussion below, a percutaneous lead will be exemplified, but it will be understood that the methods and systems described herein are also applicable to paddle leads and other leads, as well as to microstimulators.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Turning to FIG. 1, one embodiment of an electrical stimulation system 10 includes one or more stimulation leads 12 and an implantable pulse generator (IPG) 14, also referred to as a "control module". The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programmed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
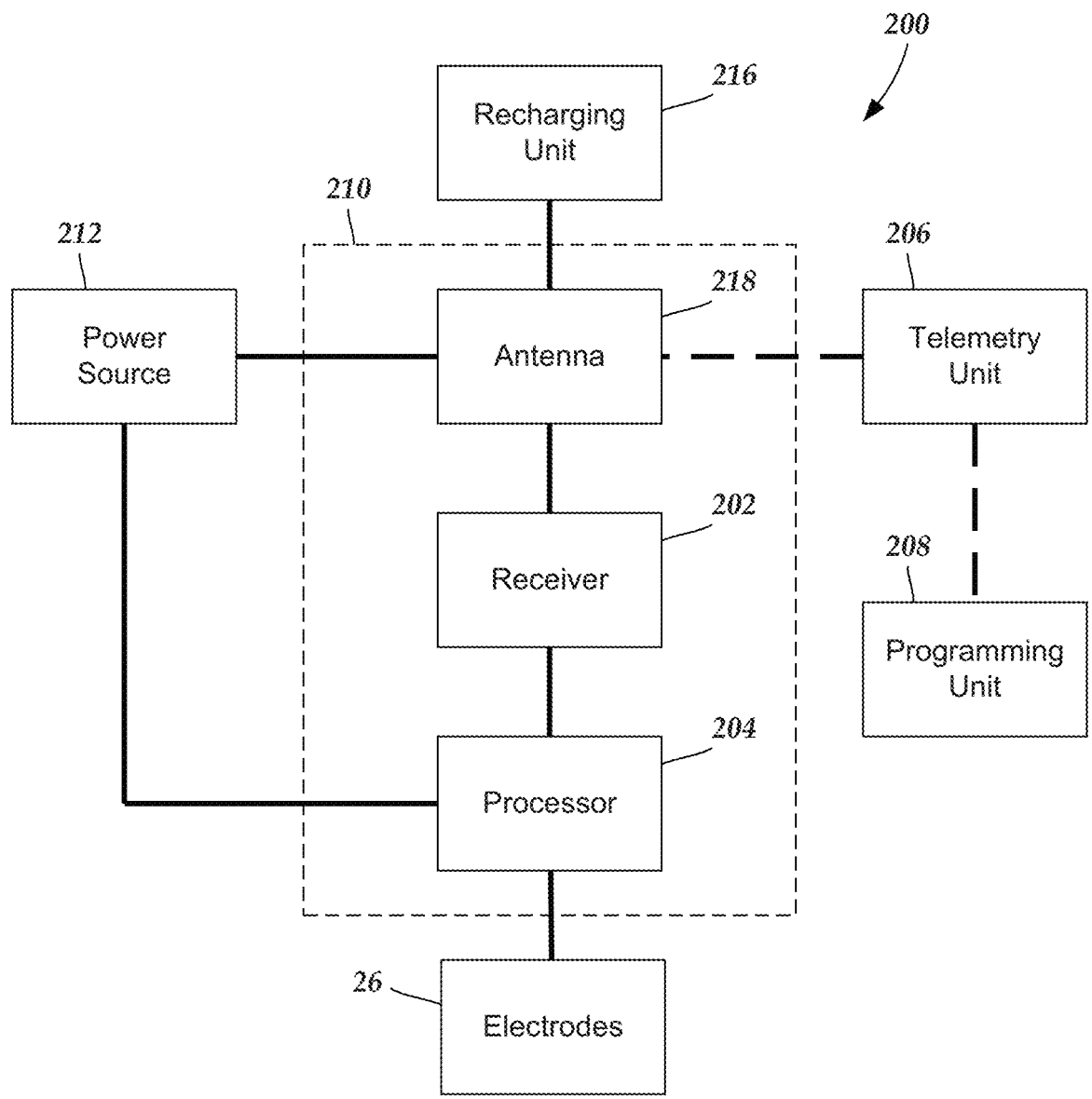
FIG. 2 is a schematic overview of one embodiment of components of a stimulation system, including an electronic subassembly disposed within a control module, according to the invention.

FIG. 2 is a schematic overview of one embodiment of components of an electrical stimulation system 200 including an electronic subassembly 210. It will be understood that the electrical stimulation system can include more, fewer, or different components and can have a variety of different configurations including those configurations disclosed in the stimulator references cited herein.

Some of the components (for example, a power source 212, an antenna 218, a receiver 202, and a processor 204) of the electrical stimulation system can be positioned on one or more circuit boards or similar carriers within a sealed housing of an IPG (see e.g., 14 in FIG. 1), if desired. Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 218 or a secondary antenna. The external power source can be in a device (e.g., a charger) positioned over the skin of the user or in a unit that is disposed near the user on a permanent or periodic basis.

If the power source 212 is a rechargeable battery, the battery may be recharged using the optional antenna 218, if desired. Power can be provided to the battery for recharging by inductively coupling the battery through the antenna to a recharging unit 216 (e.g., a charger) external to the user. Examples of such arrangements can be found in the references identified above. The electronic subassembly 210 and, optionally, the power source 212 can be disposed within the control module (e.g., the IPG 14 of FIG. 1).

In one embodiment, electrical stimulation signals are emitted by electrodes (e.g., 26 of FIG. 1) disposed on the paddle or lead body to stimulate nerve fibers, muscle fibers, or other body tissues near the electrical stimulation system. The processor 204 is generally included to control the timing and electrical characteristics of the electrical stimulation system. For example, the processor 204 can, if desired, control one or more of the timing, frequency, strength, duration, and waveform of the pulses. In addition, the processor 204 can select which electrodes can be used to provide stimulation, if desired. In some embodiments, the processor 204 selects which electrode(s) are cathodes and which electrode(s) are anodes. In some embodiments, the processor 204 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 208 that, for example, allows modification of pulse characteristics. In the illustrated embodiment, the processor 204 is coupled to a receiver 202 which, in turn, is coupled to the optional antenna 218. This allows the processor 204 to receive instructions from an external source to, for example, direct the pulse characteristics and the selection of electrodes, if desired.

In one embodiment, the antenna 218 is capable of receiving signals (e.g., RF signals) from an external telemetry unit 206 which is programmed by the programming unit 208. The programming unit 208 can be external to, or part of, the telemetry unit 206. The telemetry unit 206 can be a device that is worn over the skin of the user or can be carried by the user and can have a form similar to a pager, cellular phone, or remote control, if desired. As another alternative, the telemetry unit 206 may not be worn or carried by the user but may only be available at a home station or at a clinician's office. The programming unit 208 can be any unit that can provide information to the telemetry unit 206 for transmission to the electrical stimulation system 200. The programming unit 208 can be part of the telemetry unit 206 or can provide signals or information to the telemetry unit 206 via a wireless or wired connection. One example of a suitable programming unit is a computer operated by the user or clinician to send signals to the telemetry unit 206.

The signals sent to the processor 204 via the antenna 218 and the receiver 202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 200 to cease operation, to start operation, to start charging the battery, or to stop charging the battery. In other embodiments, the stimulation system does not include the antenna 218 or receiver 202 and the processor 204 operates as programmed.

Optionally, the electrical stimulation system 200 may include a transmitter (not shown) coupled to the processor 204 and the antenna 218 for transmitting signals back to the telemetry unit 206 or another unit capable of receiving the signals. For example, the electrical stimulation system 200 may transmit signals indicating whether the electrical stimulation system 200 is operating properly or not or indicating when the battery needs to be charged or the level of charge remaining in the battery. The processor 204 may also be capable of transmitting information about the pulse characteristics so that a user or clinician can determine or verify the characteristics.

Figure 3:
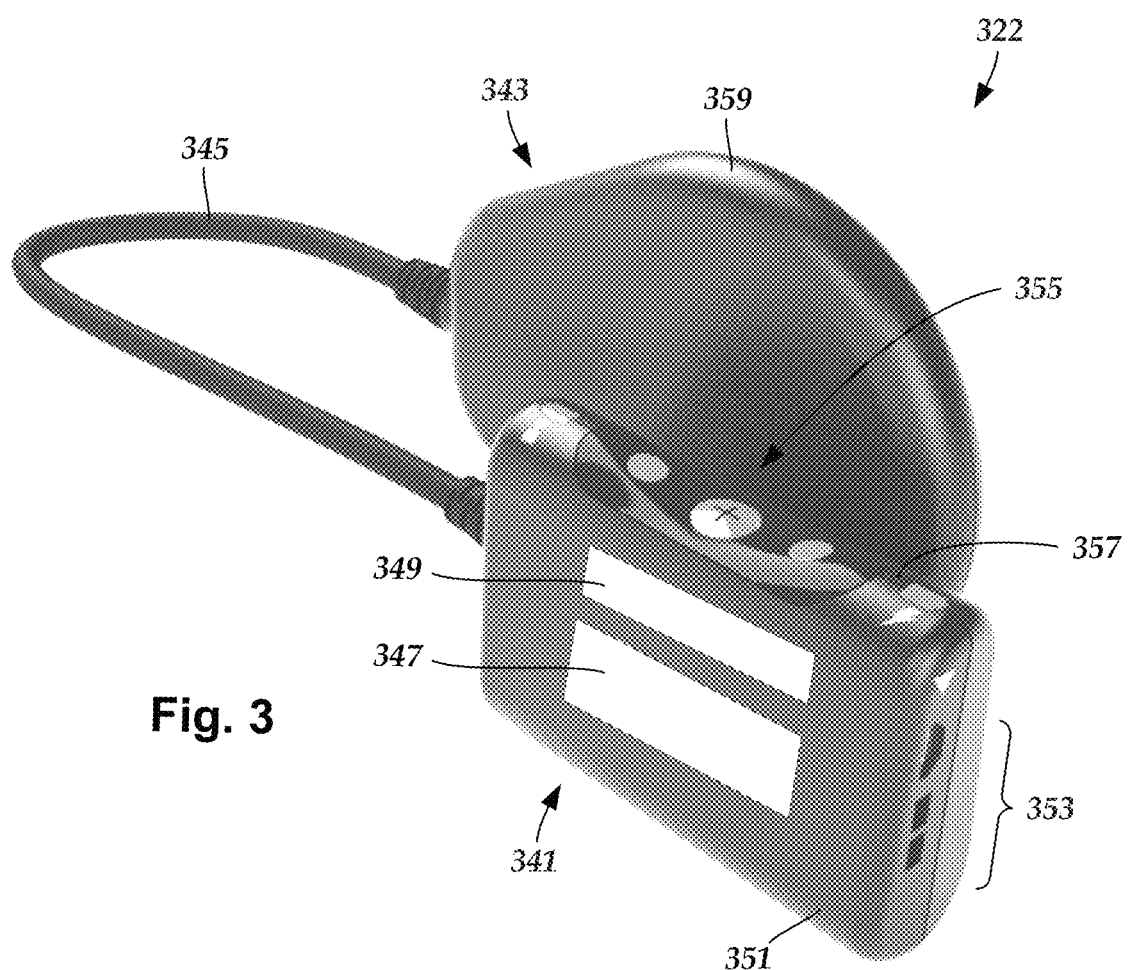
FIG. 3 is a schematic perspective view of one embodiment of a charger that includes a controller and a coil assembly, the charger suitable for recharging an implantable medical device, according to the invention.

Turning to FIG. 3, in the discussion below an implantable medical device will be exemplified by an IPG, but it will be understood that the methods and systems described herein are also applicable to other implantable medical devices with rechargeable power sources.

As described above, an implantable medical device (e.g., IPG 14 of FIG. 1) may include a rechargeable battery (e.g., power source 212 of FIG. 2) that is rechargeable via a charger (e.g., charger 22 of FIG. 1). One technique for recharging the battery of an IPG when the IPG is implanted in a patient includes using a charger to inductively recharge the IPG battery. For example, the charger may include a coil that generates a magnetic charging field that induces a current within a coil within the IPG which, in turn, charges the IPG battery.

FIG. 3 shows, in perspective view, one embodiment of a charger 322. The charger 322 includes a charger controller ("controller") 341 and a charger coil assembly ("coil assembly") 343. The coil assembly 343 includes a coil disposed in a coil housing 359. The controller 341 includes an electronics subassembly 349 disposed in a controller housing 351. An optional power source 347 (e.g., one or more batteries) may also be disposed in the controller housing 351. One or more inputs 353 (e.g., a USB port for receiving a USB cable for recharging the battery 347 of the controller) may, optionally, extend through the controller housing.

In at least some embodiments, an optional charger cable 345 couples the coil assembly 343 to the controller 341. It may be advantageous to physically separate the coil from other components of the charger, as the coil may heat up to temperatures that are potentially dangerous for one or more components of the charger (e.g., the electronics subassembly, the optional power source, or other components) during operation.

A user interface 355 is disposed along an outer surface of the controller housing. The user interface 355 includes one or more controls, such as an ON/OFF control. The user interface 355 may further include one or more indicators, such as an alignment indicator, a power-level indicator, and a charging status indicator. In at least some embodiments, the one or more indicators includes at least one visual indicator, such as one or more lights (e.g., LEDs) suitable for being seen by a patient during operation of the charger (e.g., during a charging session). In at least some embodiments, the one or more indicators includes at least one aural indicator, such as one or more speakers configured to produce one or more audible signals suitable for being heard by a patient during operation of the charger.

In at least some embodiments, one or more of the indicators of the user interface 355 are disposed along a top surface 357 of the controller housing. As will be described below and shown in at least some of the figures, the below-described wearable article is configured such that, when the controller is disposed in the wearable article and the wearable article is worn by the patient, the top surface 357 of the housing is positioned along an anterior portion of the patient and oriented towards the patient's face, thereby facilitating the ability of the patient to see and/or hear the one or more indicators and/or see or physically interact with the one or more controls while wearing the wearable article.

Recharging a power source for an implanted medical device (e.g., an IPG battery) using a charger typically includes positioning the charger coil over the patient's skin (and, optionally, over one or more layers of clothing) in proximity to the IPG, to ensure that the IPG coil is within the magnetic field generated by the charger coil, and maintaining the positioning of the charger coil relative to the implanted medical device for an amount of time sufficient to recharge the power source of the implanted medical device.

The location of the implanted medical device may not always be conducive to use of the user interface of the controller. In the case of spinal cord stimulation, the IPG is commonly implanted on or around the patient's buttocks. Thus, use of the user interface may be facilitated by positioning the user interface at a location that is more easily viewed, heard, and/or physically reached by one or more of the patient's hands. Accordingly, it may be advantageous to physically separate the charger coil from the user interface. In which case, operation of the user interface may be facilitated by positioning the user interface along an anterior portion of the patient at a location that is easily viewed, heard, and/or physically reached by one or more of the patient's hands, while enabling the charger coil to be positioned in proximity to the implanted medical device.

Figure 4A:
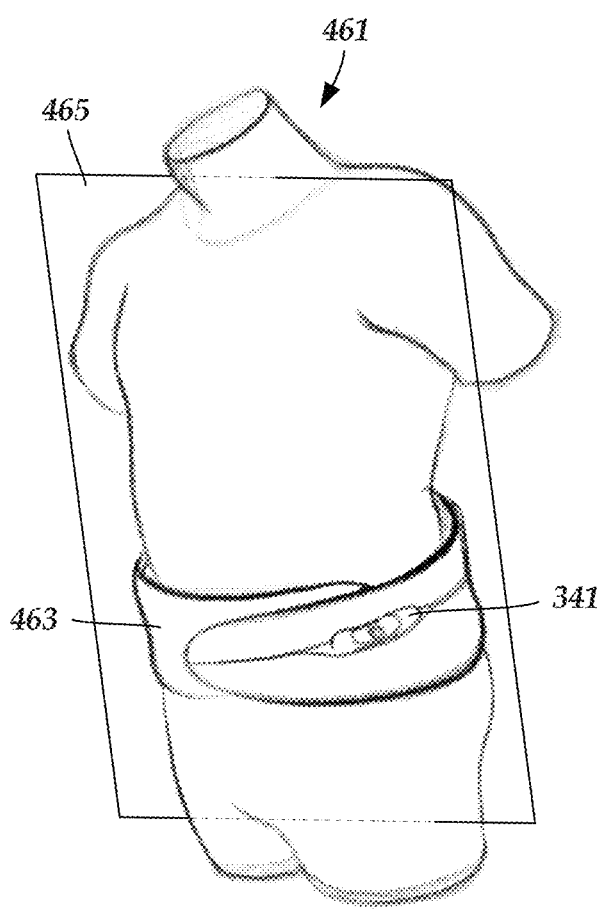
FIG. 4A is a schematic perspective view of one embodiment of a patient wearing a wearable article formed as a belt suitable for retaining the charger of FIG. 3, the belt worn in a first orientation, according to the invention.
Figure 4B:
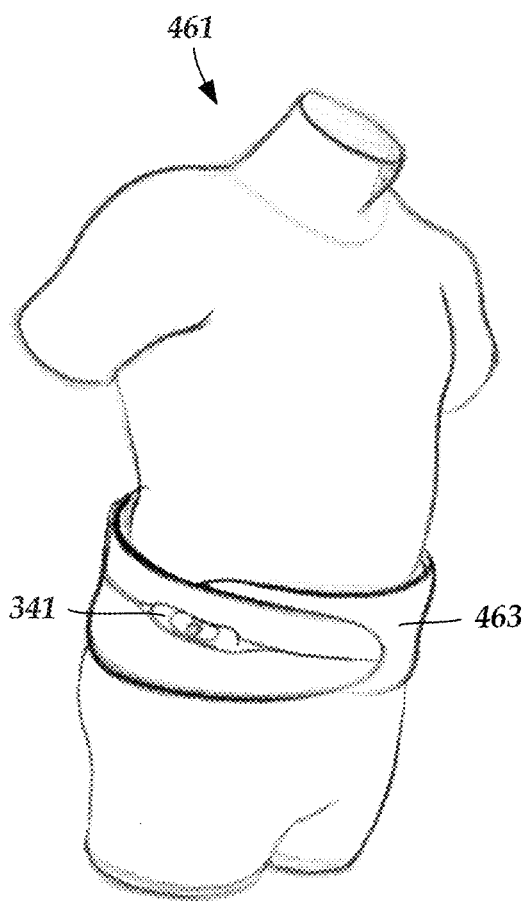
FIG. 4B is a schematic perspective view of the patient of FIG. 4A wearing the belt of FIG. 4A in a second orientation that is upside-down from the orientation shown in FIG. 4A, according to the invention.

Turning to FIGS. 4A-4B, a wearable article may be used to retain the charger coil of the coil assembly in proximity to an implanted medical device over a period of time sufficient to recharge a power source of the implanted medical device. Additionally, the wearable article can be used to retain the controller in a position that enables the user interface of the controller to be coupled to the charger coil, and also be one or more of viewable, hearable, and/or physically reachable by one or more of the patient's hands. The wearable article can vary in size, or shape, or both depending on the location of the IPG. Some types of stimulation, such as spinal cord stimulation, may include implanting an IPG in, or in proximity, to the patient's buttocks or abdomen. Many other locations within a patient are possible.

In the discussion below, a belt suitable for being worn around the waist of the patient will be exemplified, but it will be understood that a wearable article can be adapted to be worn around other portions of the patient's body including, for example, an upper extremity, lower extremity, head, neck, chest, shoulder, abdomen, or the like.

At least some conventional belts sufficient for retaining a charger suffer from shifting of the charger coil relative to the patient during operation (e.g., a charging session). For example, the charger coil may slide relative to the belt, the belt may slide or form undesired gaps or folds relative to the patient during patient movement, or some combination thereof. Shifting of the charger coil relative to the patient may undesirably increase the amount of time needed to recharge the IPG, or cause a charge to be undesirably interrupted, and even discontinued. Additionally, at least some conventional charger belts are formed from materials that are unpleasant to patients when worn directly against the patient's skin.

As herein described, a comfortable, form-fitting wearable article is described. The described wearable article is formed as a belt configured to be worn around a portion of the patient so as to position the coil assembly in close proximity to an implanted IPG while positioning the controller along an anterior portion of the patient. The coil assembly is positioned along the belt so as to reduce, or even eliminate, movement relative to the belt during operation. The belt is additionally formed to reduce, or even eliminate movement of the belt relative to the patient during patient movement. The belt can be used by patients of various shapes, sizes, ages, and genders. Moreover, the belt can be lightweight, thin, cool, comfortable, and discrete.

FIGS. 4A-4B show, in perspective views, several embodiments of a patient 461 wearing a wearable article 463 formed as a belt suitable for being worn around the waist of the patient and retaining a charger suitable for charging an implantable medical device. In at least some embodiments, the charger includes a controller and a coil assembly disposed in separate housings (e.g., charger 322 of FIG. 3). As shown in both FIGS. 4A-4B, the controller 341 is retained in the belt 463 such that the controller 341 is disposed along an anterior portion of the patient 461. In FIG. 4A, the charger is shown disposed anterior to a coronal plane 465 extending approximately along an anterior/posterior midline of the patient 461.

The belt can be worn with the controller positioned to the patient's left side, right side, or sagittal midline. In at least some embodiments, the belt is symmetrical about an axis formed along a longitudinal length and can be worn in several different orientations. For example, in FIG. 4A the belt 463 is shown being worn in a first orientation with the controller positioned along a left flank of the patient, while FIG. 4B shows the belt being worn in a second orientation, opposite to the first orientation, with the controller positioned along a right flank of the patient.

As will be described below, the belt has a front side and an opposing rear side. In some embodiments, the belt can be flipped over (with the front and rear sides remaining constant relative to the patient while being worn), thereby enabling the charger to be positioned along either side of the patient depending on the orientation of the belt when worn. Additionally, in at least some embodiments the belt is configured so that the controller is insertable into the belt in two opposing orientations relative the belt so that the controller can be disposed in the belt with a user interface (355 in FIG. 3) of the controller oriented towards the patient's face while the belt is worn around the patient's waist regardless of whether the belt is in the first orientation (FIG. 4A) or the second orientation (FIG. 4B). In at least some embodiments, the belt is symmetrical about an axis extending along a longitudinal length of the belt.

Figure 5A:
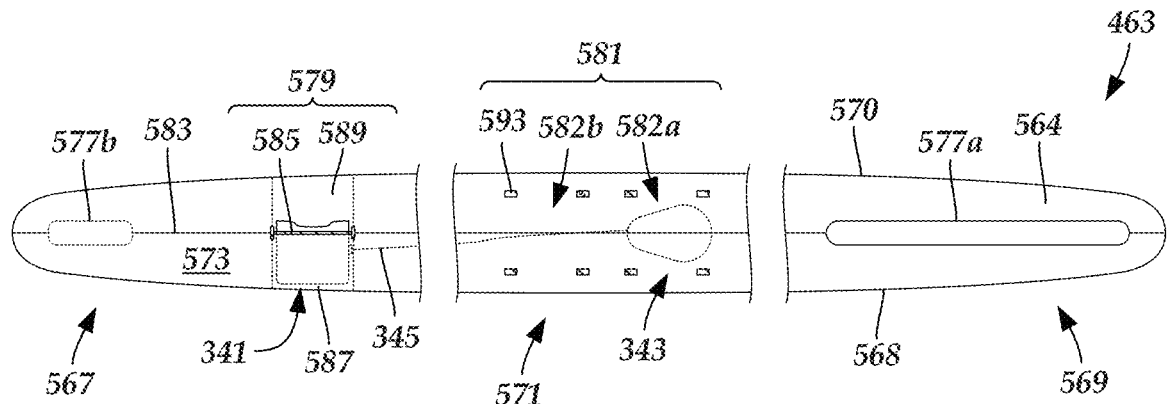
FIG. 5A is a schematic front view of one embodiment of the belt of FIG. 4A being worn in the first orientation of FIG. 4A and retaining the charger of FIG. 3, the belt including a controller slit open to two different controller cavities, each of the two controller cavities retaining the controller of the charger in a different orientation so that a user interface of the controller faces towards a patient's head when the patient wears the belt regardless of whether the belt is worn in the first or second orientation, according to the invention.
Figure 5B:
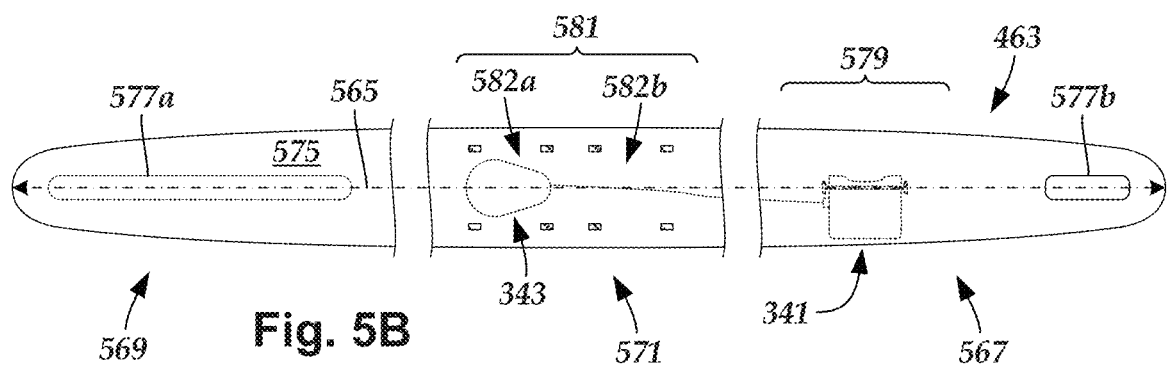
FIG. 5B is a schematic rear view of one embodiment of the belt of FIG. 5A, according to the invention.

FIG. 5A shows, in schematic front view, one embodiment of the controller 341 and the coil assembly 343 of the charger (322 in FIG. 3) disposed in the belt 463 (as depicted in FIG. 4A). FIG. 5B shows the belt 463 (as depicted in FIG. 4A) in rear view, with the controller 341 and coil assembly 343 disposed in the belt. The belt 463 is suitable for being worn by the patient (e.g., around the patient's waist) either over or beneath clothing.

The belt 463 has an elongated body 564 with a longitudinal length 565, a first end portion 567, an opposing second end portion 569, and an intermediate portion 571 disposed between the first and second end portions. The belt has a front side 573 (i.e., a first major surface) and an opposing rear side 575 (i.e., a second major surface). The front side 567 faces away from the patient when the belt is worn, while the rear side 569 faces inward to the patient when the belt is worn. Opposing first and second edges 568, 570, respectively, extend around a perimeter of the belt and separate the front and rear sides from one another.

Any suitable fastening assembly can be used to hold the belt in position along the patient while being worn. The belt may, for example, include one or more fasteners 577a, 577b (e.g., hook and loop fasteners, magnets, or the like) disposed along the opposing end portions 567, 569, respectively, to facilitate retention of the belt around the patient. In at least some embodiments, the fasteners 577a, 577b are disposed along opposing sides 573, 575, respectively. Utilizing non-buckle types of fasteners may be advantageous to increase the ease of donning and doffing the belt. Utilizing non-buckle types of fasteners may also be advantageous to simplify manufacturing and reduce costs.

The belt can have any shape suitable for being worn around the waist of a patient. In at least some embodiments, the belt 463 has an elliptical shape. An elliptical shape works well for adjusting to contours of a variety of differently-sized and differently-shaped patients. Accordingly, an elliptical shape may be conducive to retaining a given position relative to the patient despite patient movements and postural changes, as well as evenly distributing tension. The belt can also have a wide width dimension transverse to the longitudinal length of the belt. A wide width may facilitate maintaining the positioning of the belt relative to the patient by increasing surface area and distributing tension. Moreover, the overall shape of the belt may facilitate a reduction in movement of the coil assembly relative to the patient and reduce the size and shapes of gaps between belt and the skin of the patient, thereby reducing, or even eliminating lapses of operation of the charger caused by misalignment of the coil assembly and the implanted IPG. In embodiments of the belt having an elliptical shape, the longitudinal length of the belt is parallel with the major axis of the ellipse.

The belt can be formed from any suitable material or combinations of material. In at least some embodiments, the belt includes a mesh material, such as one or more 3-D spacer fabrics. In at least some embodiments, the mesh material is formed from polyester. In at least some embodiments, at least a portion of the front side, the rear side, or both, of the belt is formed from a mesh material. In at least some embodiments, one or more portions of the belt are formed from at least three layers of material, where at least one of the layers is internal (i.e., between the front and rear sides of the belt), and where the at least one internal layer is formed from mesh material.

In at least some embodiments, the belt includes an athletic or performance knit fabric. In at least some embodiments, the athletic or performance knit fabric includes polyester and one or more elastic, synthetic fibers, such as a polyether-polyurea copolymer (e.g., spandex). In at least some embodiments, at least a portion of the front side, the rear side, or both, of the belt is formed from an athletic or performance knit fabric. It may be advantageous to incorporate such material into the design of the belt to provide a thin, soft, attractive, nice-to-touch fabric along one or more exterior surfaces (i.e., front and rear sides 573, 575, respectively) of the belt. In at least some embodiments, the athletic or performance knit fabric is disposed over the mesh material exclusively along the front side of the belt. In at least some embodiments, the athletic or performance knit fabric is disposed over the mesh material exclusively along the rear side of the belt. In at least some embodiments, the athletic or performance knit fabric is disposed over the mesh material along both the front and rear sides of the belt.

In at least some embodiments, the belt is stretchable. It may be advantageous to design the belt to be stretchable to potentially provide a more snug and secure fit than a rigid belt to decrease gaps between the belt and the patient to increase patient comfort, reduce migration of the belt relative to the patient, and potentially reduce the distance between the coil assembly and the implanted IPG.

In some embodiments, the belt is configured to stretch at least 4%, 5%, 6%, 7%, 8, 9%, 10%, 11%, 12% along at least one dimension. In some embodiments, the belt is configured to stretch no more than 12%, 11%, 10%, 9%, 8%, 7%, 6%, 5%, 4%, along at least one dimension. In some embodiments, the belt is configured to stretch at least 4% and no more than 12% along at least one dimension. In some embodiments, the belt is configured to stretch at least 6% and no more than 10% along at least one dimension.

In some embodiments, the belt is configured to stretch at least 4%, 5%, 6%, 7%, 8, 9%, 10%, 11%, 12% along a longitudinal length of the belt. In some embodiments, the belt is configured to stretch no more than 12%, 11%, 10%, 9%, 8%, 7%, 6%, 5%, 4%, along a longitudinal length of the belt. In some embodiments, the belt is configured to stretch at least 4% and no more than 12% along a longitudinal length of the belt. In some embodiments, the belt is configured to stretch at least 6% and no more than 10% along a longitudinal length of the belt.

In at least some embodiments, the belt is worn with the first and second end portions disposed anteriorly along the patient (see e.g., FIGS. 4A-4B). In at least some embodiments, when the first and second end portions are disposed anteriorly along the patient, the intermediate portion 571 is disposed posteriorly along the patient. The belt, however, can be worn by a patient in any suitable rotational orientation, as desired.

The belt includes one or more controller-receiving regions 579 suitable for receiving and retaining the controller 341. As mentioned above, it is typically advantageous for the controller to be disposed anteriorly along the patient while the belt is worn. Accordingly, in at least some embodiments the one or more controller-receiving regions 579 are disposed on one or more of the first or second end portions 567, 569. In FIG. 5A (and in other figures), the controller-receiving region 579 is shown disposed along the first end portion 567 of the belt.

The belt further includes one or more coil-assembly-receiving regions 581 suitable for receiving the coil assembly. As mentioned above, implanted IPGs are often positioned along the belt so that, when the belt is worn by a patient, the coil assembly is disposed posteriorly along the patient. Accordingly, in at least some embodiments the one or more coil-assembly-receiving regions are disposed along the intermediate portion 571.

The controller and/or the coil assembly can either be removable from the belt or permanently disposed on or in the belt. In FIGS. 5A-5B, the controller is shown as being removable from the belt while the coil assembly (as well as portion, or all, of the charger cable 345) is permanently disposed in the belt. Other figures show both the controller and coil assembly being removable from the belt. It may be advantageous to incorporate one or more of the coil assembly and charger cable into the belt to make the belt, coil assembly, and/or charger cable an integrated unit for simplicity of use, and also to conceal the coil assembly and/or charger cable from view to facilitate providing a discreet charging session.

In at least some embodiments, the belt includes a longitudinal seam 583 extending along at least a portion of the longitudinal length of the belt. In some embodiments, the belt includes a single longitudinal seam. In other embodiments, the belt includes multiple longitudinal seams. In at least some embodiments, the longitudinal seam extends along the entire longitudinal length of the belt. In FIG. 5A (and in other figures), the belt is shown as being elliptical with the longitudinal seam extending along the major axis of the ellipse. In some embodiments, the longitudinal seam 583 is disposed along the front side of the belt. In other embodiments, the longitudinal seam 583 extends along the rear side of the belt. In some embodiments, the longitudinal seam 583 extends along both the front and rear sides of the belt.

In some embodiments, the belt is symmetrical about the longitudinal seam. As described below, in at least some embodiments the longitudinal seam is used for providing access to the controller, the coil assembly, or both, via one or more slits formed along the longitudinal seam. It may be advantageous to form the belt to be symmetrical about the longitudinal seam to facilitate adaptability of the belt to be worn in opposing orientations (see e.g., FIGS. 4A-4B) while aligning the coil assembly with an implanted medical device. It may also be advantageous for the belt to have a width dimension (transverse to the longitudinal length) long enough to enable the controller to be inserted into the belt via a slit defined along the longitudinal length along two opposing directions, depending on the orientation of the belt while being worn.

In at least some embodiments, zigzag stitching is used along one or more seams (e.g., the longitudinal seam, the first edge, the second edge, between multiple panels of material disposed along one or more of the sides of the belt, or the like or combinations thereof). In some embodiments, zigzag stitching is used along an entire perimeter of the belt. The zigzag stitching may facilitate the stretchability of the belt which, in turn, may provide a more snug and secure fit to decrease gaps between the belt and the patient to increase patient comfort, reduce migration of the belt relative to the patient, and potentially reduce the distance between the coil assembly and the implanted IPG.

One or more slits can be formed along one or more of the first and second sides. In some embodiments, one or more slits are formed along one or more portions of the longitudinal seam. The one or more slits open to one or more cavities formed between the front and rear sides of the belt that are adapted to enable the controller, coil assembly, or both to pass into or out of the one or more cavities.

In FIG. 5A, a controller slit 585 is shown formed along a portion of the longitudinal seam along the controller-receiving region 579. The controller slit 585 is configured to receive the controller and provide access to each of a first controller cavity 587 and a second controller cavity 589 disposed between the front and rear sides of the belt. In at least some embodiments, the controller slit 585 extends in a direction that is parallel, or approximately parallel, to the longitudinal length of the belt.

The first and second controller cavities at least partially overlap one another along the longitudinal length of the body to enable the same controller slit to be used to provide access to each of the controller cavities. In some embodiments, the controller slit 585 is disposed along the first end portion of the belt. In other embodiments, the controller slit 585 is disposed along the second end portion of the belt. In some embodiments, controller slits are disposed along each of the first and second end portions of the belt.

In some embodiments, the first controller cavity 587 extends from the controller slit towards (or to) the first edge 568 of the belt. In some embodiments, the second controller cavity 589 extends from the controller slit towards (or to) the second edge 570 of the belt. Accordingly, the controller can be inserted through the controller slit and into either the first controller cavity 587 or the second controller cavity 589, depending on how (i.e., in which orientation) the belt is to be worn. When the controller is inserted into the first controller cavity 587, the user interface (355 in FIG. 3) of the controller faces towards the patient's head when the belt is worn around the patient's waist, as depicted in FIG. 4A. Conversely, when the controller is inserted into the second controller cavity 589, the user interface faces towards the patient's head when the belt is worn around the patient's waist, as depicted in FIG. 4B.

In at least some embodiments, the first controller cavity 587 is formed such that, when the controller is placed into the first controller cavity, the user interface (355 in FIG. 3) is disposed external to the first controller cavity. Similarly, in at least some embodiments the first controller cavity 587 is formed such that, when the controller is placed into the second controller cavity, the user interface (355 in FIG. 3) is disposed external to the second controller cavity.

Such a design may facilitate providing access to the user interface. When the user interface is positioned externally from the controller cavities, the user interface can be easily accessible to facilitate interaction from the patient. In some instances, a patient may not want to see the user interface when not physically interacting with it. Accordingly, in some embodiments the user interface can, optionally, be tucked into the opposing controller cavity, as desired. For example, when the controller is disposed in the first controller cavity, the user interface of the controller can either be positioned external to the belt, or can be tucked into the second controller cavity to obscure the user interface from the patient's view.

The first controller cavity and/or the optional second controller cavity can be physically separate from one another, or can be different portions of the same cavity. In some embodiments, the first and second controller cavities are at least partially separated from one another by the longitudinal seam. In some embodiments, the first controller cavity and/or the optional second controller cavity are bound along one or both sides by stitching (shown in FIG. 5A by dotted lines extending transversely from the longitudinal seam 583 on either side of the controller cavities 587, 589) to reduce, or even prevent, shifting of the controller relative to the belt.

Figure 5C:
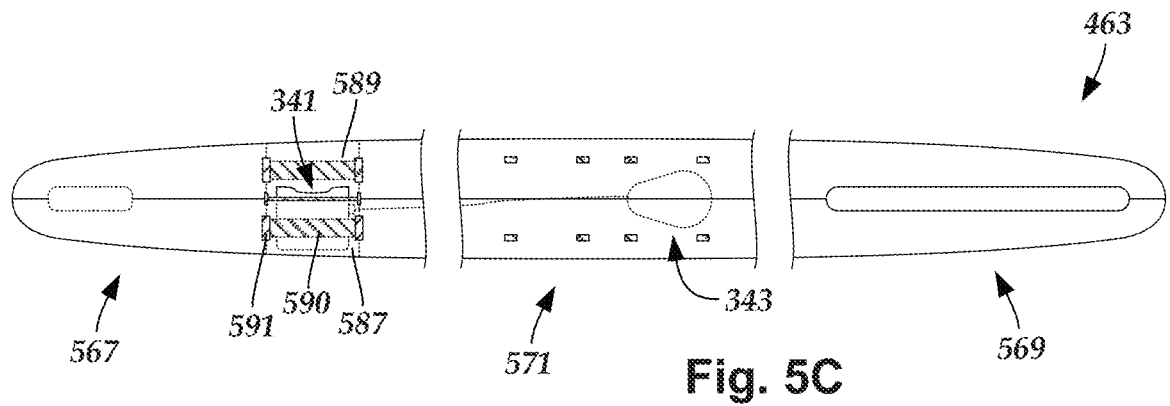
FIG. 5C is a schematic front view of another embodiment of the belt of FIG. 5A, according to the invention.

Turning briefly to FIG. 5C, in at least some embodiments one or more elastic bands, such as elastic band 590, are disposed along one or more of the controller cavities 587, 589 of the belt, either inside or outside the controller cavities. The one or more elastic bands may facilitate retention of the controller and reduce the potential for undesired movement of the controller relative to the belt while the belt is being worn by a patient. In some embodiments, the one or more elastic bands are used in lieu of the one or more cavities to retain the controller. In at least some embodiments, box stitching, such as box stitch 591, is used to couple the ends of the elastic bands to the belt.

Turning back to FIGS. 5A-5B, as mentioned above the belt includes one or more coil-assembly-receiving regions suitable for receiving the coil assembly 343. As mentioned above, during a recharging session the coil assembly is disposed in proximity to the implanted medical device (e.g., an IPG). Accordingly, the location of the coil-assembly-receiving region corresponds to the portion of the belt closest to the implanted medical device when the belt is worn by the patient.

In FIG. 5A, a coil-assembly-receiving region 581 is shown disposed along the intermediate portion 571 of the belt. In some embodiments, at least one coil-assembly-receiving region is disposed along one, or both, of the end portions 567, 569 of the belt. The one or more coil-assembly-receiving regions can define one or more coil-assembly cavities suitable for retaining a coil assembly (e.g., coil assembly 343 of FIG. 3). In FIGS. 5A-5B (and in other figures), two coil-assembly cavities 582a, 582b, are shown. The coil-assembly cavities 582a, 582b are shown offset from one another along the longitudinal length of the belt. In some embodiments with multiple coil-assembly cavities, the cavities are offset from one another along a direction transverse to the longitudinal seam in addition to, or in lieu of, being offset along the longitudinal length of the belt.

The coil assembly can be either permanently disposed in one of the coil-assembly cavities, or be removable from one or more coil-assembly cavities. In FIGS. 5A-5C (and in other figures), the coil assembly is shown permanently disposed in one of the coil-assembly cavities. In some embodiments, the one or more coil-assembly cavities include one or more features to limit, or even prevent, movement of the coil assembly relative to the belt when the coil assembly is disposed within the belt. In at least some embodiments, one or more bartacks, such as bartack 593, are used to define one or more boundaries (e.g., corners) of one or more of the coil-assembly cavities. In some embodiments, a single bartack is utilized. In other embodiments, multiple bartacks are utilized. In FIGS. 5A-5C (and in other figures) each of the one or more coil-assembly-receiving regions includes four bartacks defining boundaries for restricting movement of the coil assembly relative to the belt. In at least some embodiments, one or more of the controller cavities include one or more bartacks.

The charger may include a charger cable (e.g., charger cable 345) coupling the controller to the coil assembly. In at least some embodiments, the charger cable extends between the coil assembly and the controller within the body 564 of the belt, between two or more layers of material. In some embodiments, the charger cable extends entirely within the body of the belt between the cavities within which the controller and coil assembly are disposed. In some embodiments, the charger cable extends substantially entirely within the body of the belt.

Figure 6A:
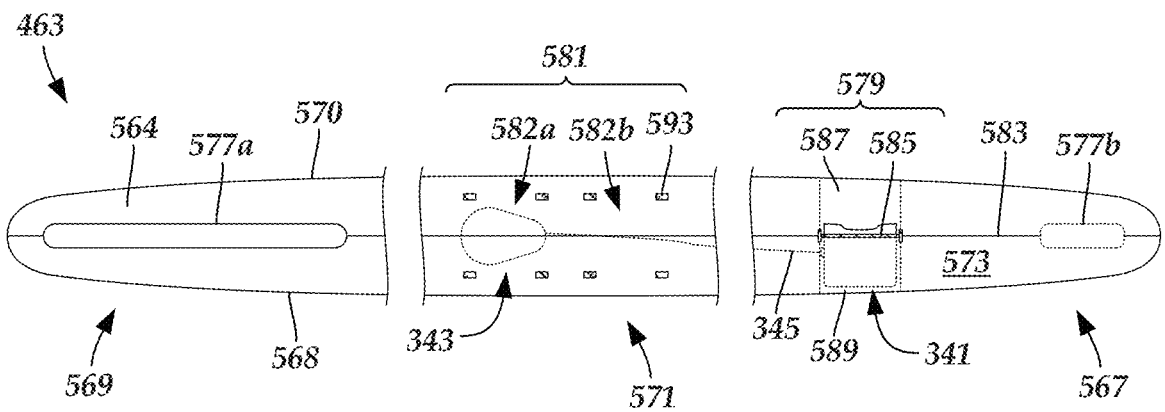
FIG. 6A is a schematic front view of one embodiment of the belt of FIG. 5A worn in the second orientation of FIG. 4B, the belt retaining the charger of FIG. 3, according to the invention.
Figure 6B:
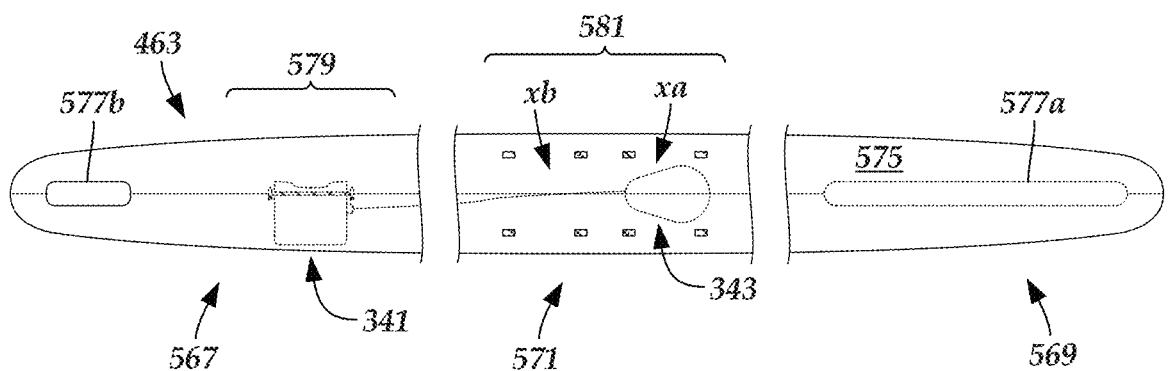
FIG. 6B is a schematic rear view of one embodiment of the belt of FIG. 6A, according to the invention.

Turning to FIGS. 6A-6B, as mentioned previously with reference to FIGS. 4A-4B, in some embodiments the belt is wearable in several different orientations. FIG. 6A shows, in schematic front view, the belt 463 in the second orientation (as depicted in FIG. 4B), where the orientation of the belt upside-down from the first orientation (as depicted in FIG. 4A and FIGS. 5A-5C). FIG. 6B shows the second orientation of the belt 463 in rear view. As shown in FIG. 6A, the controller 341 is no longer disposed in the first controller cavity 587, as shown in FIG. 5A. Instead, the controller is flipped over from the orientation shown in FIG. 5A and inserted into the second controller cavity 589.

It may be advantageous to enable the belt to be wearable in multiple different orientations to potentially increase the number of locations along the patient the controller and coil assembly can be positioned during use. As shown in FIGS. 4A-4B, the two different orientations enable the controller to be disposed on either side of the patient. This may be especially advantageous if the patient has difficulty seeing, hearing, or interacting with the user interface along one side of their body.

With regards to the coil assembly, providing multiple wearable orientations of the belt enables the coil assembly to be positioned at two different bilateral locations along a patient by merely flipping over the belt, without needing to move the coil assembly from one coil-assembly cavity to another. Accordingly, the same belt can be used by two different patients where, for example, one of the patients has an IPG implanted into his or her left buttock and the other of the two patients has an IPG implanted into his or her right buttock. Thus, the coil assembly can, in some embodiments, be permanently disposed in the belt and be used by patients with an IPG implanted into either of two different bilateral locations.

Figure 7A:
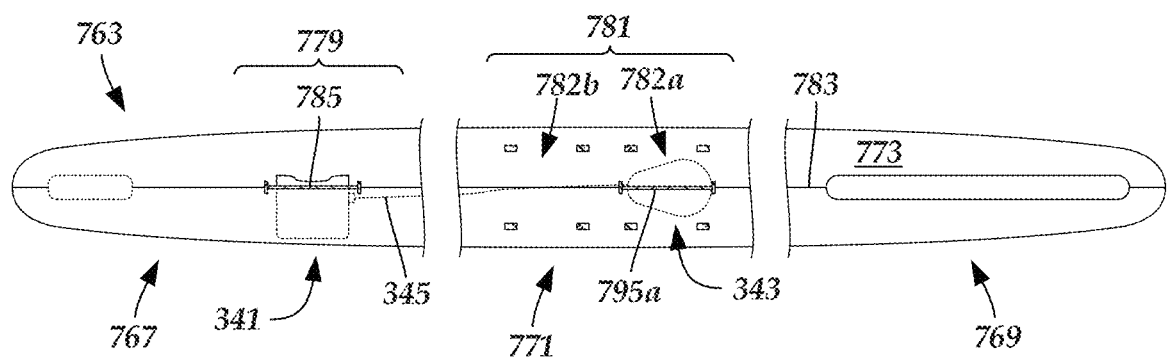
FIG. 7A is a schematic front view of another embodiment of a belt retaining the charger of FIG. 3, the belt including two coil-assembly cavities each suitable for retaining the coil assembly of the charger of FIG. 3, the belt also defining a coil-assembly slit positioned to enable the coil assembly to be inserted exclusively into one of the two coil-assembly cavities, according to the invention.
Figure 7B:
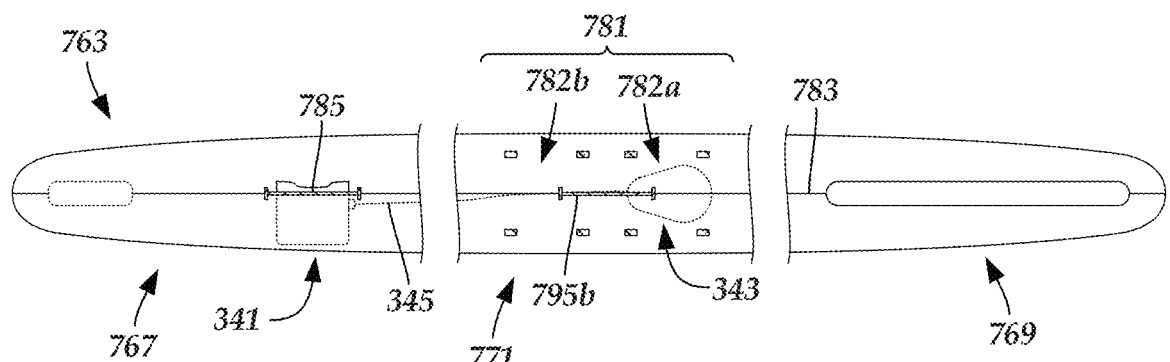
FIG. 7B is a schematic front view of another embodiment of the belt of FIG. 7A, the belt including a coil-assembly slit open to each of two differently-positioned coil-assembly cavities and positioned to enable the coil assembly of the charger of FIG. 3 to be inserted into either of the two coil-assembly cavities, according to the invention.

Turning to FIGS. 7A-7B, in some embodiments the coil assembly is removable from the belt. FIGS. 7A-7B show, in schematic front view, several alternate embodiments of a belt 763 suitable for retaining the controller 341, the coil assembly 343 and, optionally, the interconnecting charger cable 345. The belt 763 is similar to the belt (463 of FIGS. 4A-6B) described above, with a first end portion 767, an opposing second end portion 769, and an intermediate portion 771 disposed between the first and second end portions. The belt has a front side 773 and an opposing rear side. Note that FIGS. 7A-7B both show the front side 773.

The belt 763 includes one or more controller-receiving regions 779 suitable for receiving and retaining the controller 341, and one or more coil-assembly-receiving regions 781 suitable for receiving the coil assembly 343. The controller-receiving region 779 shown in FIGS. 7A-7B is positioned along the first end portion 767 of the belt and can include one or more controller cavities suitable for retaining the controller in one or more different orientations, as described above. In FIGS. 7A-7B, the coil-assembly-receiving region 781 is positioned along the intermediate portion 771 of the belt and includes two coil-assembly cavities 782a, 782b longitudinally-offset from one another along a longitudinal length of the belt.

Multiple slits are formed along one or more portions of the front side 773 of the belt (e.g., along a longitudinal seam 783). The slits are adapted to enable the controller, the coil assembly, or both, to pass into one or more cavities defined in the belt. In FIG. 7A, a controller slit 785 is shown formed along a portion of the longitudinal seam along the controller-receiving region 779 and is configured to receive a controller (e.g., controller 341 of FIG. 3), as described above with reference to FIGS. 5A-5C.

The belt 763 further defines one or more coil-assembly slits that open to one or more of the coil-assembly cavities 782a, 782b and enable a coil assembly (e.g., coil assembly 343 of FIG. 3) to be passed into or out of one or more of the coil-assembly cavities 782a, 782b. In FIG. 7A, a coil assembly slit 795a is shown disposed along the controller-receiving region 779 over the coil-assembly cavity 782a and is configured to enable the coil assembly to be passed into or out of the coil-assembly cavity 782a without enabling the coil assembly to access the coil-assembly cavity 782b. In alternate embodiments, the coil-assembly slit 795a is disposed over the coil-assembly cavity 782b and is configured to enable the coil assembly to be passed into or out of the coil-assembly cavity 782b without enabling the coil assembly to access the coil-assembly cavity 782a. In FIG. 7B, a coil assembly slit 795b is shown disposed along the controller-receiving region 779 over each of the coil-assembly cavities 782a, 782b and is configured to enable the coil assembly to be passed into or out of either of the coil-assembly cavities 782a, 782b.

Figure 8A:
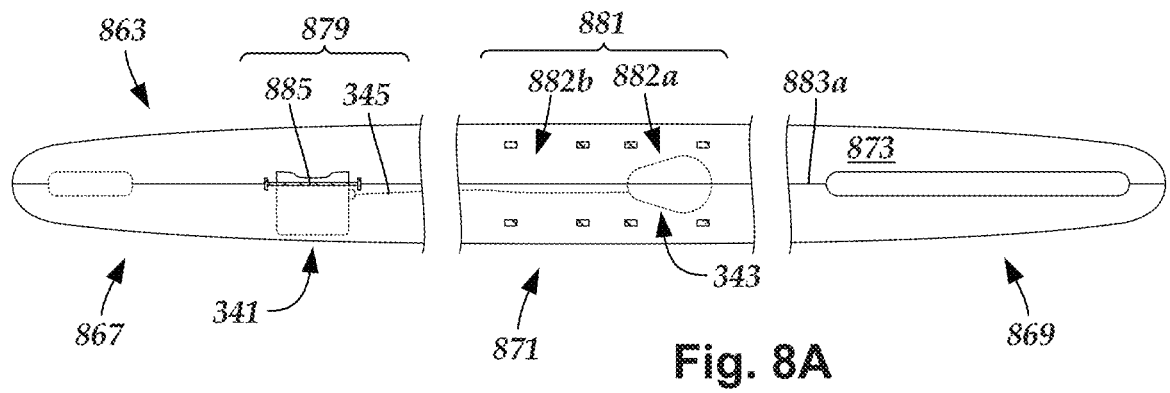
FIG. 8A is a schematic front view of another embodiment of a belt suitable for retaining the charger of FIG. 3, the belt defining a controller slit formed along a front side of the belt and open to one or more controller cavities defined in the belt and suitable for receiving a controller of the charger of FIG. 3, the belt also defining a coil-assembly slit formed along a rear side of the belt and open to one or more of two coil-assembly cavities defined in the belt and suitable for receiving a coil assembly of the charger of FIG. 3, according to the invention.
Figure 8B:
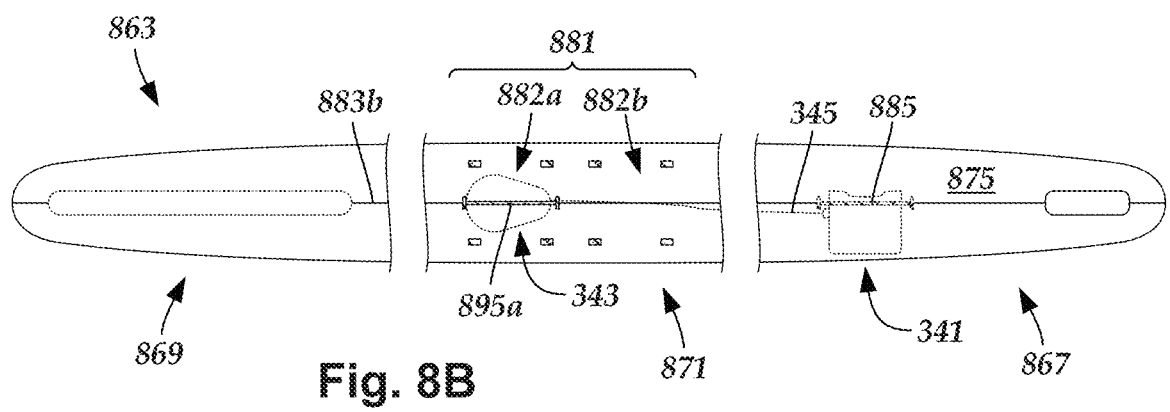
FIG. 8B is a schematic rear view of one embodiment of the belt of FIG. 8A with a coil-assembly slit positioned to enable the coil assembly to be inserted exclusively into one of the two coil-assembly cavities, according to the invention.

Turning to FIGS. 8A-8B, in the previous embodiments the one or more slits were all defined along front side of the belt. In some embodiments, one or more slits are defined along the rear side of the belt. In some embodiments, one or more slits are defined along each of the front and rear sides of the belt. FIG. 8A shows, in schematic front view, another embodiment of a front side 873 of a belt 863 suitable for retaining the controller 341, the coil assembly 343 and, optionally, the interconnecting charger cable 345. The belt 863 is similar to the belt (463 of FIGS. 4A-6B) described above, with a first end portion 867, an opposing second end portion 869, and an intermediate portion 871 disposed between the first and second end portions.

The belt 863 includes one or more controller-receiving regions 879 suitable for receiving and retaining the controller 341, and one or more coil-assembly-receiving regions 881 suitable for receiving the coil assembly 343. The controller-receiving region 879 shown in FIG. 8A is positioned along the first end portion 867 of the belt and can include one or more controller cavities suitable for retaining the controller in one or more different orientations, as described above. A controller slit 885 is formed within the controller-receiving region 779 along one or more portions of the front side 873 of the belt (e.g., along a longitudinal seam 883a) and is configured to receive a controller (e.g., controller 341 of FIG. 3), as described above with reference to FIGS. 5A-5C.

In FIG. 8A, the coil-assembly-receiving region 881 is positioned along the intermediate portion 871 of the belt and includes two coil-assembly cavities 882a, 882b longitudinally-offset from one another along a longitudinal length of the belt. The coil assembly 343 can be disposed in either of the coil-assembly cavities. In FIG. 8A, the coil assembly 343 is shown disposed in the coil-assembly cavity 882a.

Figure 8C:
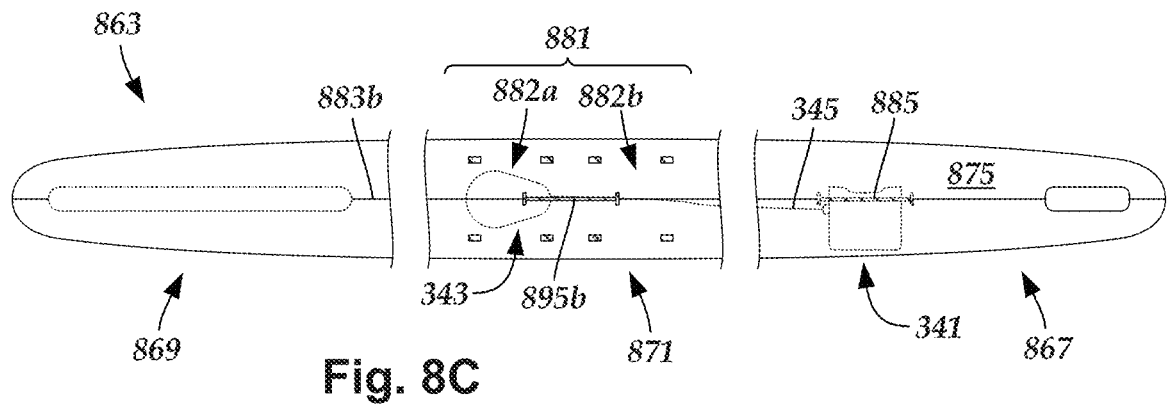
FIG. 8C is a schematic rear view of another embodiment of the belt of FIG. 8A with a coil-assembly slit positioned to enable the coil assembly to be inserted into either of two coil-assembly cavities, according to the invention.

FIGS. 8B-8C show two alternate views of a rear side 875 of the belt 863, opposite to the front side 873 shown in FIG. 8A. In each of FIGS. 8B-8C, a coil-assembly slit is formed along the rear side 875 of the belt 863 and provides access to one or more of the coil-assembly cavities 882a, 882b. It may be advantageous to position the coil-assembly slit along the rear side of the belt to reduce the risk of the coil assembly being undesirably dislodged from the belt through the slit when the belt is being worn by the patient.

In FIG. 8B, a coil assembly slit 895a is shown disposed along the rear side 875 of the belt 863 in the controller-receiving region 879 over the coil-assembly cavity 882a and is configured to enable the coil assembly to be passed into or out of the coil-assembly cavity 882a without enabling the coil assembly to access the coil-assembly cavity 882b. In alternate embodiments, the coil-assembly slit 895a is disposed along the rear side 875 of the belt 863 over the coil-assembly cavity 882b and is configured to enable the coil assembly to be passed into or out of the coil-assembly cavity 882b without enabling the coil assembly to access the coil-assembly cavity 882a. In FIG. 8C, a coil assembly slit 895b is shown disposed along the rear side 875 of the belt 863 in the controller-receiving region 879 over each of the coil-assembly cavities 882a, 882b and is configured to enable the coil assembly to be passed into or out of either of the coil-assembly cavities 882*a*, 882*b*.

Figure 9A:
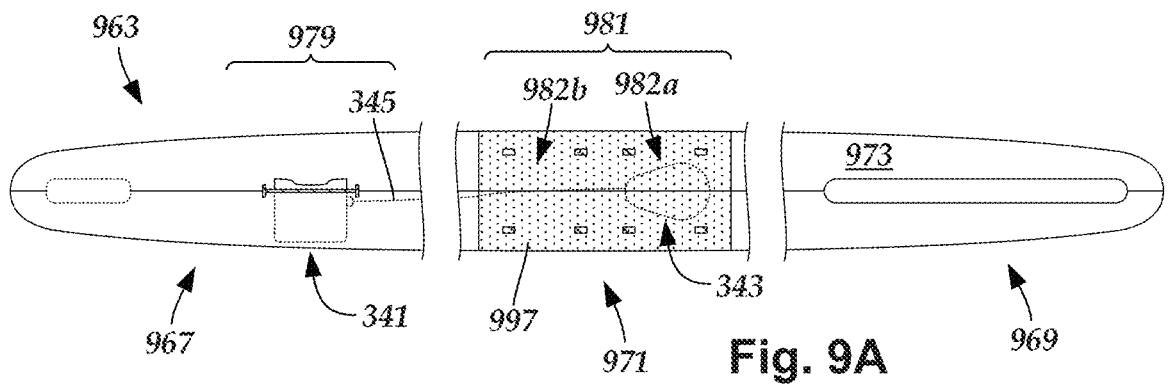
FIG. 9A is a schematic front view of another embodiment of a belt suitable for retaining the charger of FIG. 3, the belt including a mesh fabric disposed along a front side of the belt along a coil-assembly-retaining portion of the belt, according to the invention.

Turning to FIGS. 9A-10B, as described above the belt can be formed from any suitable material(s) including, for example, one or more of a mesh material and an athletic or performance knit fabric. FIGS. 9A-10B show several different embodiments of incorporation of a mesh material into the design of the belt. FIG. 9A shows, in schematic front view, another embodiment of a front side 973 of a belt 963 suitable for retaining the controller 341, the coil assembly 343 and, optionally, the interconnecting charger cable 345. The belt 963 is similar to the belt (463 of FIGS. 4A-6B) described above, with a first end portion 967, an opposing second end portion 969, and an intermediate portion 971 disposed between the first and second end portions.

The belt 963 includes one or more controller-receiving regions 979 suitable for receiving and retaining the controller 341, and one or more coil-assembly-receiving regions 981 suitable for receiving the coil assembly 343. The controller-receiving region 979 shown in FIG. 9A is positioned along the first end portion 967 of the belt and can include one or more controller cavities suitable for retaining the controller in one or more different orientations, as described above. In FIG. 9A, the coil-assembly-receiving region 981 is positioned along the intermediate portion 971 of the belt and includes two coil-assembly cavities 982*a*, 982*b* longitudinally-offset from one another along a longitudinal length of the belt. The coil assembly 343 can be disposed in either of the coil-assembly cavities. In FIG. 9A, the coil assembly 343 is shown disposed in the coil-assembly cavity 982*a*.

As shown in FIG. 9A by a stippled region, the front side 973 of the coil-assembly-receiving region 981 is formed from a mesh material 997, such as one or more 3-D spacer fabrics. The mesh material 997 may provide cushioning and smooth out body contours. Additionally, it may be advantageous to incorporate such material into the design of the belt, particularly along the front side of the belt, to facilitate dissipation of heat (e.g., heat produced by the coil assembly during operation) and provide breathability to the belt. The mesh material may, for example, enable the patient to sit with the coil assembly disposed between the patient and a back of a chair without the patient getting burned or potentially damaging the chair or the patient's clothing. Moreover, such fabric may also provide comfort, heft, and cushion for the patient when wearing the belt.

Figure 9B:
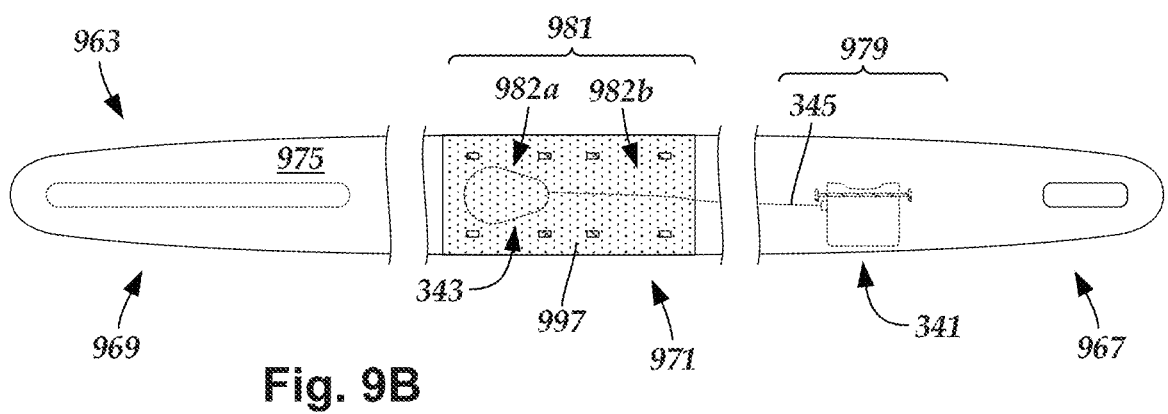
FIG. 9B is a schematic rear view of one embodiment of the belt of FIG. 9A, the belt including mesh fabric disposed along both front and rear sides of the belt along a coil-assembly-retaining portion of the belt, according to the invention.
Figure 9C:
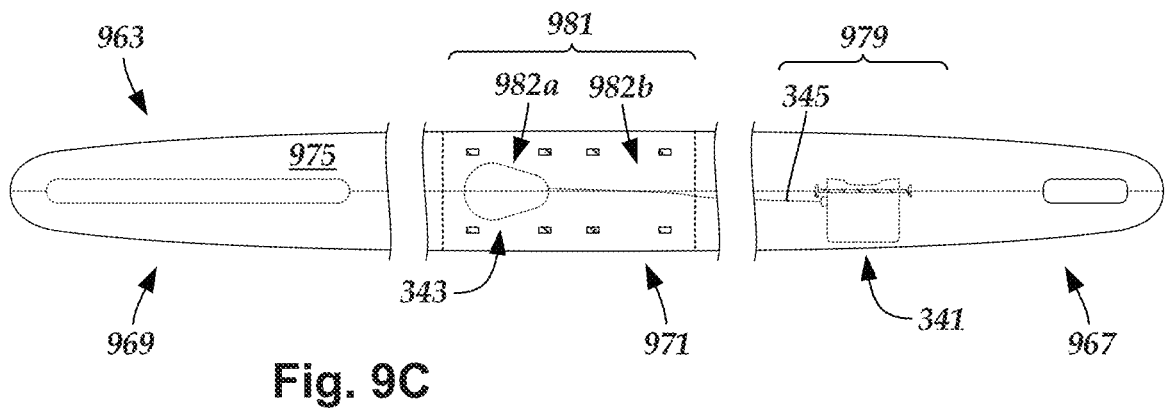
FIG. 9C is a schematic rear view of another embodiment of the belt of FIG. 9A, the belt including a mesh fabric disposed along a front side of the belt along a coil-assembly-retaining portion of the belt, but not along a rear side of the belt along the coil-assembly-retaining portion, according to the invention.

The mesh material 997 can be disposed along both the front and rear sides of the belt along the coil-assembly-receiving region, or be disposed exclusively along the front side of the belt along the coil-assembly-receiving region. FIGS. 9B-9C show two alternate views of a rear side 975 of the belt 963, opposite to the front side 973 shown in FIG. 9A. In FIG. 9B, the rear side 975 of the coil-assembly-receiving region 981 is shown as also being formed from the mesh material 997. In FIG. 9C, the rear side 975 of the coil-assembly-receiving region 981 is shown as being formed from a material other than the mesh material such as, for example, one or more athletic or performance knit fabrics.

Figure 10A:
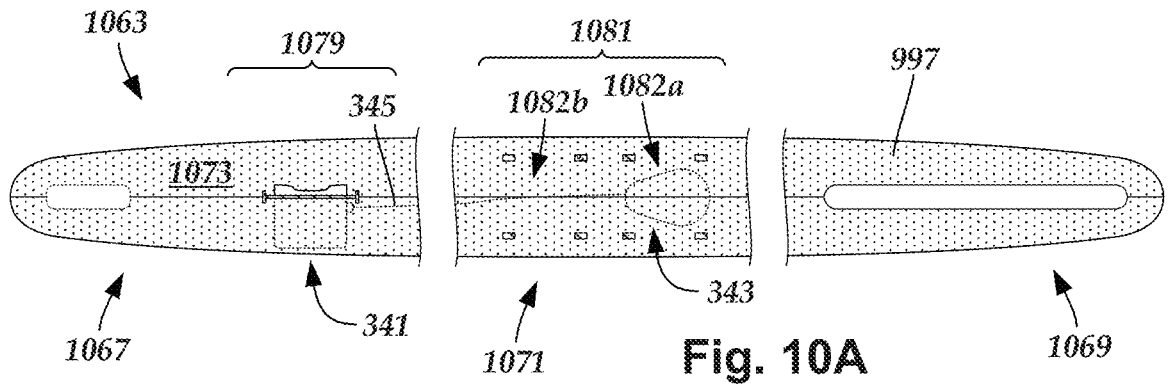
FIG. 10A is a schematic front view of another embodiment of a belt suitable for retaining the charger of FIG. 3, the belt including a mesh fabric disposed over an entire front side of the body of the belt, according to the invention.

The mesh material can be disposed exclusively along the coil-assembly-receiving region, or can be additionally disposed along one or more other portions of the belt. In some embodiments, the mesh material is disposed along the entire front side, rear side, or both the front and rear sides of the belt. FIG. 10A shows, in schematic front view, another embodiment of a front side 1073 of a belt 1063 suitable for retaining the controller 341, the coil assembly 343 and, optionally, the interconnecting charger cable 345. The belt 1063 is similar to the belt (463 of FIGS. 4A-6B) described above, with a first end portion 1067, an opposing second end portion 1069, and an intermediate portion 1071 disposed between the first and second end portions.

The belt 1063 includes one or more controller-receiving regions 1079 suitable for receiving and retaining the controller 341, and one or more coil-assembly-receiving regions 1081 suitable for receiving the coil assembly 343. The controller-receiving region 1079 shown in FIG. 10A is positioned along the first end portion 1067 of the belt and can include one or more controller cavities suitable for retaining the controller in one or more different orientations, as described above. In FIG. 10A, the coil-assembly-receiving region 1081 is positioned along the intermediate portion 1071 of the belt and includes two coil-assembly cavities 1082*a*, 1082*b* longitudinally-offset from one another along a longitudinal length of the belt. The coil assembly 343 can be disposed in either of the coil-assembly cavities. In FIG. 10A, the coil assembly 343 is shown disposed in the coil-assembly cavity 1082*a*.

In at least some embodiments, the controller-receiving region 1079 and the coil-assembly-receiving region 1081 are both formed from the mesh material 997. In some embodiments, and as shown in FIG. 10A, the entire front side 1073 of the belt 1063 is formed from the mesh material 997.

Figure 10B:
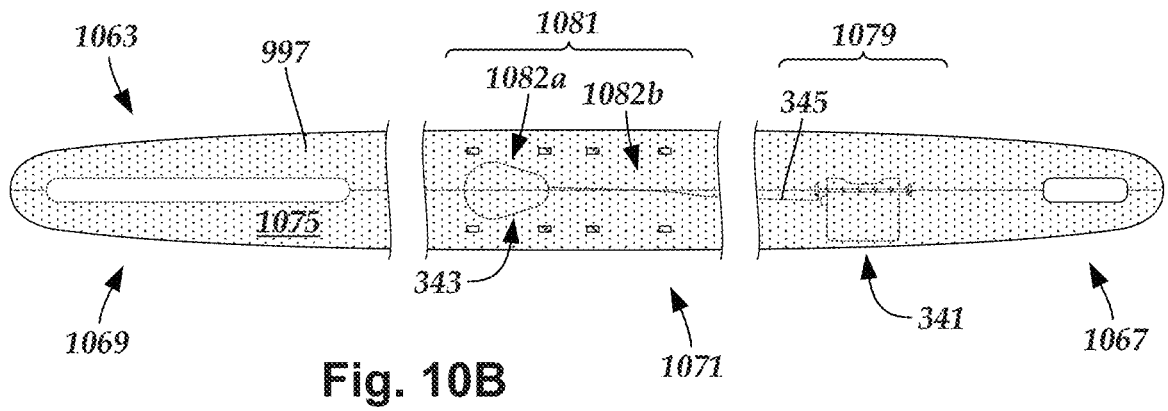
FIG. 10B is a schematic rear view of one embodiment of the belt of FIG. 10A, the belt including a mesh fabric disposed over an entire front side of the belt and also disposed over an entire rear side of the belt, according to the invention.
Figure 10C:
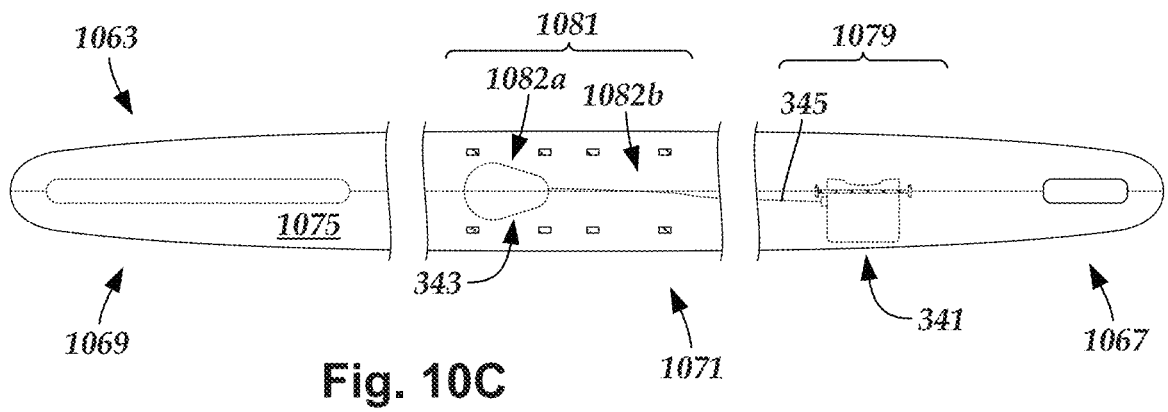
FIG. 10C is a schematic rear view of another embodiment of the belt of FIG. 10A, the belt including a mesh fabric disposed over an entire front side of the belt and not disposed along a rear side of the belt, according to the invention.

The mesh material 997 can be disposed along both the front and rear sides of the belt, or be disposed exclusively along the front side of the belt. FIGS. 10B-10C show two alternate views of a rear side 1075 of the belt 1063, opposite to the front side 1073 shown in FIG. 10A. In FIG. 10B, the rear side 975 of the entire body of the belt 1063 is shown as also being formed from the mesh material 997. In FIG. 10C, the rear side 1075 of belt 1063 is shown as being formed from a material other than the mesh material such as, for example, one or more athletic or performance knit fabrics.

Figure 11:
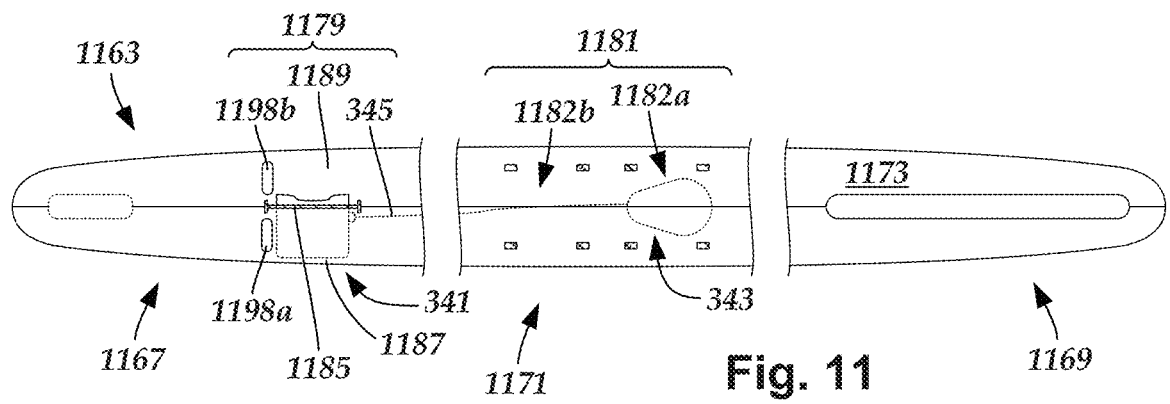
FIG. 11 is a schematic front view of another embodiment of a belt suitable for retaining the charger of FIG. 3, the belt including one or more utility apertures in proximity to one or more controller cavities defined in the belt for receiving a controller of the charger, the one or more utility apertures suitable for at least one of a) enabling a charging cable to be coupled to the controller while the controller is disposed in the controller cavity, or b) for enhancing the ability of a patient wearing the belt to hear auditory signals emitted from the controller when the controller is disposed in one of the controller cavities, according to the invention.

Turning to FIG. 11, in some embodiments one or more utility apertures are defined in proximity to the one or more controller cavities. FIG. 11 shows, in schematic front view, another embodiment of a front side 1173 of a belt 1163 suitable for retaining the controller 341, the coil assembly 343 and, optionally, the interconnecting charger cable 345. The belt 1163 is similar to the belt (463 of FIGS. 4A-6B) described above, with a first end portion 1167, an opposing second end portion 1169, and an intermediate portion 1171 disposed between the first and second end portions.

The belt 1163 includes one or more controller-receiving regions 1179 suitable for receiving and retaining the controller 341, and one or more coil-assembly-receiving regions 1181 suitable for receiving the coil assembly 343. The controller-receiving region 1179 shown in FIG. 11 is positioned along the first end portion 1167 of the belt and can include one or more controller cavities suitable for retaining the controller via one or more controller slits 1185 in one or more different orientations, as described above. In FIG. 11, the coil-assembly-receiving region 1181 is positioned along the intermediate portion 1171 of the belt and includes two coil-assembly cavities 1182*a*, 1182*b* longitudinally-offset from one another along a longitudinal length of the belt. The coil assembly 343 can be disposed in either of the coil-assembly cavities. In FIG. 11, the coil assembly 343 is shown disposed in the coil-assembly cavity 1182*a*.

The belt 1163 defines one or more utility apertures along the controller-retaining portion of the belt. In FIG. 11, two utility apertures 1198*a*, 1198*b* are shown. In some embodiments, the utility apertures extend between the front side 1173 of the belt and the one or more controller cavities 1187, 1189. In some embodiments, the utility apertures extend between the rear side of the belt and the one or more of the controller cavities. In some embodiments, the utility apertures extend to one or more of the controller cavities from both the front and rear sides of the belt.

In some embodiments, the one or more utility apertures are suitable for enabling a cable (e.g., a charging cable) to be coupled to the controller from a location external to the belt while the controller is disposed in one of the controller cavities. It may be advantageous to enable a cable to extend into the controller disposed in the controller cavity to enable the controller to be charged without removing the controller from the belt (e.g., during a charging session).

In some embodiments, the one or more utility apertures are suitable for facilitating the ability of a patient wearing the belt to hear auditory signals emitted from the controller. As also mentioned above, the user interface of the controller may include one or more indicators, such as an alignment indicator, a power-level indicator, and a charging status indicator. The indicator(s) may include one or more aural indicators, such as one or more speakers, configured to produce one or more audible signals suitable for being heard by a patient during operation of the charger.

As also mentioned above, in some embodiments the user interface can, optionally, be tucked into the opposing controller cavity. For example, when the controller is disposed in the first controller cavity, the user interface of the controller can be tucked into the second controller cavity to obscure the user interface from the patient's view. Unfortunately, obscuring the user interface with the fabric of the belt may reduce the ability of the patient to hear audible alerts. Accordingly, the one or more utility apertures are suitable for facilitating the ability of a patient wearing the belt to hear auditory signals emitted from the controller.

Figure 12:
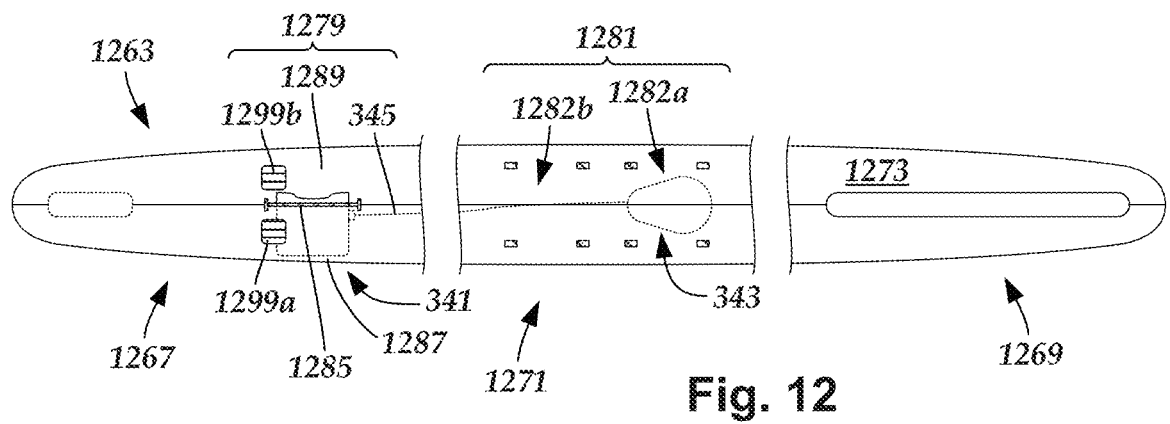
FIG. 12 is a schematic front view of another embodiment of a belt suitable for retaining the charger of FIG. 3, the belt including one or more perforated regions in proximity to one or more controller cavities defined in the belt for receiving a controller of the charger, the one or more perforated regions suitable for enhancing the ability of a patient wearing the belt to hear auditory signals emitted from the controller when the controller is disposed in one of the controller cavities, according to the invention.

Turning to FIG. 12, in some embodiments one or more perforated regions are defined in proximity to the one or more controller cavities. FIG. 12 shows, in schematic front view, another embodiment of a front side 1273 of a belt 1263 suitable for retaining the controller 341, the coil assembly 343 and, optionally, the interconnecting charger cable 345. The belt 1263 is similar to the belt (463 of FIGS. 4A-6B) described above, with a first end portion 1267, an opposing second end portion 1269, and an intermediate portion 1271 disposed between the first and second end portions.

The belt 1263 includes one or more controller-receiving regions 1279 suitable for receiving and retaining the controller 341, and one or more coil-assembly-receiving regions 1281 suitable for receiving the coil assembly 343. The controller-receiving region 1279 shown in FIG. 12 is positioned along the first end portion 1267 of the belt and can include one or more controller cavities suitable for retaining the controller via one or more controller slits 1285 in one or more different orientations, as described above. In FIG. 12, the coil-assembly-receiving region 1281 is positioned along the intermediate portion 1271 of the belt and includes two coil-assembly cavities 1282a, 1282b longitudinally-offset from one another along a longitudinal length of the belt. The coil assembly 343 can be disposed in either of the coil-assembly cavities. In FIG. 12, the coil assembly 343 is shown disposed in the coil-assembly cavity 1282a.

The belt 1263 defines one or more perforated regions along the controller-retaining portion of the belt. In FIG. 12, two perforated regions 1299a, 1299b are shown. In some embodiments, the perforated regions extend between the front side 1273 of the belt and the one or more controller cavities 1287, 1289. In some embodiments, the perforated regions extend between the rear side of the belt and the one or more of the controller cavities. In some embodiments, the perforated regions extend to one or more of the controller cavities from both the front and rear sides of the belt.

In some embodiments, the one or more perforated regions are suitable for facilitating the ability of a patient wearing the belt to hear auditory signals emitted from the controller. As also mentioned above, the user interface of the controller may include one or more indicators, such as an alignment indicator, a power-level indicator, and a charging status indicator. The indicator(s) may include one or more aural indicators, such as one or more speakers, configured to produce one or more audible signals suitable for being heard by a patient during operation of the charger.

As also mentioned above, in some embodiments the user interface can, optionally, be tucked into the opposing controller cavity. For example, when the controller is disposed in the first controller cavity, the user interface of the controller can be tucked into the second controller cavity to obscure the user interface from the patient's view. Unfortunately, obscuring the user interface with the fabric of the belt may reduce the ability of the patient to hear audible alerts. Accordingly, the one or more perforated regions are suitable for facilitating the ability of a patient wearing the belt to hear auditory signals emitted from the controller.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A wearable article for receiving and retaining a charger for charging a medical device implanted into a patient, the charger comprising a coil assembly and a controller with a controller housing and a user interface disposed along the controller housing, the wearable article comprising:
   a body having an elongated shape with a longitudinal length, a first major surface, and an opposing second major surface, wherein the first major surface is configured and arranged for facing outwardly from the patient when the wearable article is worn by the patient;
   a coil-assembly cavity defined in the body between the first major surface and the second major surface and configured and arranged to retain the coil assembly;
   a first controller cavity defined in the body between the first major surface and the second major surface and configured and arranged to receive a first portion of the controller housing;
   a second controller cavity defined in the body between the first major surface and the second major surface and configured and arranged to receive a second portion of the controller housing; and
   a controller slit defined along the first major surface and open to both the first controller cavity and the second controller cavity;
   wherein the first controller cavity is configured and arranged to receive the first portion of the controller housing with the user interface extending or observable through the controller slit or disposed in the second controller cavity, wherein the body is further configured and arranged for a charger cable to extend from the coil assembly to the controller housing of the controller within a cable cavity that extends between the first major surface and the second major surface and between the coil-assembly cavity and the first controller cavity.

2. The wearable article of claim 1, wherein the first and second controller cavities are positioned along the body so that they are both disposed along an anterior portion of the patient when the wearable article is worn by the patient with the coil-assembly cavity positioned at least partially over a medical device implanted in the patient.

3. The wearable article of claim 1, wherein the coil-assembly cavity permanently retains the coil assembly.

4. The wearable article of claim 1, further comprising a coil-assembly slit configured and arranged for user removal of the coil assembly from the coil-assembly cavity.

5. The wearable article of claim 1, wherein the coil-assembly cavity is a first coil-assembly cavity and further comprising a second coil-assembly cavity offset from the first coil-assembly cavity along the longitudinal length of the body, the second coil-assembly cavity configured and arranged to retain the coil assembly.

6. The wearable article of claim 5, further comprising a coil-assembly slit, the coil-assembly slit open to each of the first coil-assembly cavity and the second coil-assembly cavity and configured and arranged to enable the coil assembly to pass through the coil-assembly slit and into either the first coil-assembly cavity or the second coil-assembly cavity.

7. The wearable article of claim 1, wherein at least one of the first major surface or the second major surface of the body along the coil-assembly cavity is formed from a mesh material.

8. The wearable article of claim 1, wherein at least one of the first major surface or the second major surface of the body along the coil-assembly cavity is formed from a performance knit fabric.

9. The wearable article of claim 1, wherein the body is configured and arranged to stretch by no less than 4% and no more than 12% along a longitudinal length of the body.

10. The wearable article of claim 1, wherein the body has an elliptical shape.

11. The wearable article of claim 1, wherein the controller slit is disposed along a longitudinal seam extending along the longitudinal length of the body along the first major surface.

12. The wearable article of claim 11, wherein the body is symmetrical about the longitudinal seam.

13. A charging system for charging a medical device implanted into a patient, the charging system comprising:
the wearable article of claim 1; and
a charger configured and arranged for being retained by the wearable article, the charger comprising
a coil assembly, and
a controller coupleable with the coil assembly, the controller comprising a battery, a controller housing, and a user interface along the controller housing;
wherein the first controller cavity of the wearable article is configured and arranged to receive a first portion of the controller housing with the user interface extending or observable through the controller slit or disposed in the second controller cavity of the wearable article with a second portion of the controller housing of the controller.

14. The charging system of claim 13, wherein the first major surface of the wearable article defines one or more utility apertures positioned in proximity to the first controller cavity of the wearable article, the one or more utility apertures configured and arranged to receive a cable from a location external to the wearable article and enable the cable to couple with the controller to charge the controller battery while the controller is at least partially retained in the first controller cavity.

15. The charging system of claim 13, wherein the first major surface of the wearable article defines one or more perforated regions positioned in proximity to the second controller cavity of the wearable article, the one or more perforated regions configured and arranged to facilitate the patient hearing audible signals output from the user interface of the controller.

16. The charging system of claim 13, wherein the charger further comprises a charger cable coupleable to the coil assembly and the controller, wherein the body of the wearable article is further configured and arranged for a charger cable to extend from the coil assembly to the controller housing of the controller in a cable cavity that extends between the first major surface and the second major surface and between the coil-assembly cavity and the first controller cavity.

17. The charging system of claim 16, wherein the charger cable is permanently retained within the body of the wearable article.

18. The charging system of claim 16, wherein the coil assembly is permanently retained within the body of the wearable article.

19. The wearable article of claim 1, wherein the first controller cavity extends from the controller slit toward a first edge of the wearable article and the second controller cavity extends from the controller slit toward a second edge of the wearable article that is opposite the first edge.

* * * * *